United States Patent
Hartley et al.

(10) Patent No.: US 7,577,479 B2
(45) Date of Patent: Aug. 18, 2009

(54) METHODS AND DEVICES FOR IMPLEMENTING TIME OF DAY PACING ADJUSTMENTS

(75) Inventors: Jesse W. Hartley, Lino Lakes, MN (US); Kent Lee, Shoreview, MN (US); Quan Ni, Shoreview, MN (US); Michael A. Querimit, Fridley, MN (US); Kenneth L. Baker, Shoreview, MN (US); Ankur Garg, Minneapolis, MN (US); Kenneth I. Tobacman, Cedar, MN (US); Corey J. Miklos, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 164 days.

(21) Appl. No.: 11/083,136

(22) Filed: Mar. 17, 2005

(65) Prior Publication Data
US 2006/0212080 A1   Sep. 21, 2006

(51) Int. Cl.
*A61N 1/365* (2006.01)
(52) U.S. Cl. .......................................................... 607/9
(58) Field of Classification Search .................... 607/9, 607/17–18, 23, 19
See application file for complete search history.

(56) References Cited

U.S. PATENT DOCUMENTS

| | | | |
|---|---|---|---|
| 4,922,930 A | 5/1990 | Adkins et al. |
| 5,065,759 A | 11/1991 | Begemann et al. |
| 5,143,065 A | 9/1992 | Adkins et al. |
| 5,733,312 A | 3/1998 | Schloss et al. |
| 5,861,011 A | 1/1999 | Stoop |
| 5,891,175 A | 4/1999 | Walmsley et al. |
| 6,128,534 A | 10/2000 | Park et al. |
| 6,161,041 A | 12/2000 | Stoop et al. |
| 6,238,422 B1 | 5/2001 | Van Oort |
| 6,823,214 B1 | 11/2004 | Sun et al. |

OTHER PUBLICATIONS

"INSIGNIA® Pacing Systems." Guidant / For Medical Professionals. Guidant Corporation, 2004, p. 1-2. Printed Sep. 17, 2004. http://www.guidant.com/products.

*Primary Examiner*—Mark W Bockelman
*Assistant Examiner*—Eric D Bertram
(74) *Attorney, Agent, or Firm*—Hollingsworth & Funk, LLC

(57) ABSTRACT

Methods and systems are directed to delivering cardiac pacing therapy to a patient. A pacing therapy associated with one or more pacing parameters is delivered. Alternate cardiac pacing therapies associated with one or more alternate pacing parameters are transitioned to, based on a sleep/wake cycle of the patient. Interactions between the pacing parameters of the pacing therapy and the alternate pacing parameters are resolved. Resolving pacing parameters may be based on analysis of lower rate limits and/or lower rate hysteresis.

11 Claims, 7 Drawing Sheets

METHODS AND DEVICES FOR IMPLEMENTING TIME OF DAY PACING ADJUSTMENTS

FIELD OF THE INVENTION

The present invention relates generally to cardiac rhythm management devices and, more particularly, to delivering, with a cardiac rhythm management device, cardiac pacing therapy with one or more cardiac pacing parameters adjusted in accordance with a patient's sleep/wake cycle.

BACKGROUND OF THE INVENTION

The healthy heart produces regular, synchronized contractions. Rhythmic contractions of the heart are normally controlled by the sinoatrial (SA) node, specialized cells located in the upper right atrium. The SA node is the normal pacemaker of the heart, typically initiating 60-100 heart beats per minute. When the SA node is pacing the heart normally, the heart is said to be in normal sinus rhythm (NSR).

If heart contractions are uncoordinated or irregular, the heart is denoted to be arrhythmic. Cardiac arrhythmia impairs cardiac efficiency and can be a potential life threatening event. Cardiac arrhythmias have a number of etiological sources including tissue damage due to myocardial infarction, infection, or degradation of the heart's ability to generate or synchronize the electrical impulses that coordinate contractions.

Bradycardia occurs when the heart rhythm is too slow. This condition may be caused, for example, by delayed impulses from the SA node, denoted sick sinus syndrome, or by a blockage of the electrical impulse between the atria and ventricles. Bradycardia produces a heart rate that is too slow to maintain adequate circulation.

When the heart rate is too rapid, the condition is denoted tachycardia. Tachycardia may have its origin in either the atria or the ventricles. Tachycardias occurring in the atria of the heart, for example, include atrial fibrillation and atrial flutter. Both conditions are characterized by rapid, uncoordinated contractions of the atria.

Ventricular tachycardia occurs, for example, when a pulse is initiated in the ventricular myocardium at a rate more rapid than the normal sinus rhythm. Ventricular tachycardia can quickly degenerate into ventricular fibrillation (VF). Ventricular fibrillation is a condition denoted by extremely rapid, nonsynchronous contractions of the ventricles. The rapid and erratic contractions of the ventricles cannot effectively pump blood to the body and the condition is fatal unless the heart is returned to sinus rhythm within a few minutes.

Implantable cardiac rhythm management systems have been used as an effective treatment for patients with serious arrhythmias. These systems typically comprise circuitry to sense signals from the heart and a pulse generator for providing electrical pulses to the heart. Leads extending into the patient's heart are connected to electrodes that contact the myocardium for sensing the heart's electrical signals and for delivering pulses to the heart in accordance with various therapies for treating the arrhythmias described above.

Pacemakers may be incorporated into cardiac rhythm management systems to deliver pace pulses to the heart. Pace pulses are low energy electrical pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing the heart. Single chamber pacemakers may pace and sense one heart chamber. A typical single chamber pacemaker is connected to a lead extending either to the right atrium or the right ventricle. Dual chamber pacemakers may pace and sense two chambers of the heart. A typical dual chamber pacemaker is typically connected to two leads, one lead extending to the right atrium and one lead to the right ventricle.

Pacemakers may be used to provide pacing pulses to both the left ventricle and the right ventricle. This type therapy may be used, for example, to coordinate ventricular contractions when a patient suffers from congestive heart failure (CHF). Congestive heart failure is a condition wherein the muscles of the heart deteriorate, causing the heart muscle to enlarge. Enlargement of the heart causes the contractile impulses to travel more slowly, resulting in asynchronous contractions of the left and right ventricles and reduced pumping efficiency.

Pacemakers can be programmed to provide pace pulses to the heart on demand or at a fixed rate. When a pacemaker paces the heart at a fixed rate, the pacemaker provides pace pulses to the heart without taking into account the heart's spontaneous action. In contrast, pacemakers may sense the spontaneous activity of the heart and provide pace pulses synchronized to the spontaneous activity.

For example, a single chamber ventricular pacemaker may sense and pace a ventricle. The pacemaker senses ventricular activity and provides a pace pulse to the ventricle if no spontaneous activity is sensed. If the pacemaker senses spontaneous activity, the pacing pulse is inhibited. In this example, where the pacemaker senses the ventricle, paces the ventricle and inhibits the ventricular pace pulse upon sensing a spontaneous R-wave, the pacemaker mode is denoted VVI. Alternatively, a single chamber pacemaker may sense and pace the atrium. In the case where the pacemaker senses the atrium, paces the atrium and inhibits the atrial pace pulse upon sensing a spontaneous P-wave, the pacemaker mode is denoted AAI.

A dual chamber pacemaker may be capable of sensing and pacing both the atrium and ventricle. The dual channel pacemaker is capable of using pace pulses to synchronize atrial and ventricular activity. If spontaneous cardiac activity is detected in the atrium or the ventricle, pacing pulses may be triggered or inhibited. When the pacemaker paces and senses both chambers and can trigger or inhibit pace pulses based upon sensed signals, for example, the pacemaker mode is denoted DDD. Various other configurations involving providing or inhibiting pace pulses based upon sensed cardiac events using dual or single chamber pacemakers are known in the art.

Rate adaptive pacemakers provide pacing at rates responsive to the patient's metabolic activity. Changes in metabolic activity may reflect exercise or non-exercise related changes, such as stress or excitement. The level of metabolic activity may be determined by sensing motion, respiratory rate, QT interval, venous oxygen saturation, temperature, or other patient conditions, for example. The pacemaker automatically adjusts the pacing rate to accommodate the sensed changes in the patient's condition.

Implantable cardioverter/defibrillators (ICDs) have been used as an effective treatment for patients with serious cardiac arrhythmias. For example, ICDs are capable of delivering high energy shocks to the heart, interrupting the ventricular tachyarrhythmia or ventricular fibrillation and allowing the heart to resume a normal rhythm. ICDs may include pacing functions described above as well as a cardioversion/defibrillation capability.

SUMMARY OF THE INVENTION

Various embodiments of present invention involve methods and systems for implementing time of day-based pacing parameter adjustments.

In one embodiment a method for delivering therapy to a patient requires delivering a cardiac pacing therapy associated with one or more pacing parameters. An alternate cardiac pacing therapy with one or more alternate pacing parameters is transitioned to based on a sleep/wake cycle of the patient. According to the embodiment, any interactions between the pacing parameters of the pacing therapy and the alternate pacing parameters are resolved.

In various embodiments of the invention, resolving interactions between pacing parameters of pacing therapies includes using an alternate lower rate limit associated with the alternate cardiac pacing therapy during the alternate pacing therapy if the alternate lower rate limit is below a lower rate limit associated with the cardiac pacing therapy.

In other embodiments, resolving interactions between pacing parameters includes using a lower rate hysteresis if the alternate lower rate limit associated with the alternate cardiac pacing therapy is below the lower rate limit associated with the cardiac pacing therapy.

In various other embodiments, resolving interactions between pacing parameters may include using a lower rate limit associated with the cardiac pacing therapy during the alternate cardiac pacing therapy if an alternate lower rate limit associated with the alternate cardiac pacing therapy is above the lower rate limit.

In another embodiment of the present invention, a cardiac rhythm management system provides one or more electrodes for electrically coupling to a heart, a pulse generator coupled to the one or more electrodes for delivering pacing pulses to the heart, circuitry for acquiring information associated with a patient's sleep/wake cycle, and a therapy controller coupled to the pulse generator and the sleep/wake circuitry. The therapy controller controls transitions between a plurality of pacing therapies based on the patient's sleep/wake cycle. Pacing therapies include a pacing therapy associated with one or more pacing parameters and an alternate pacing therapy associated with one or more alternate pacing parameters. The therapy controller additionally includes an arbitration processor configured to resolve interactions between the pacing parameters of the pacing therapy and the alternate pacing parameters.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
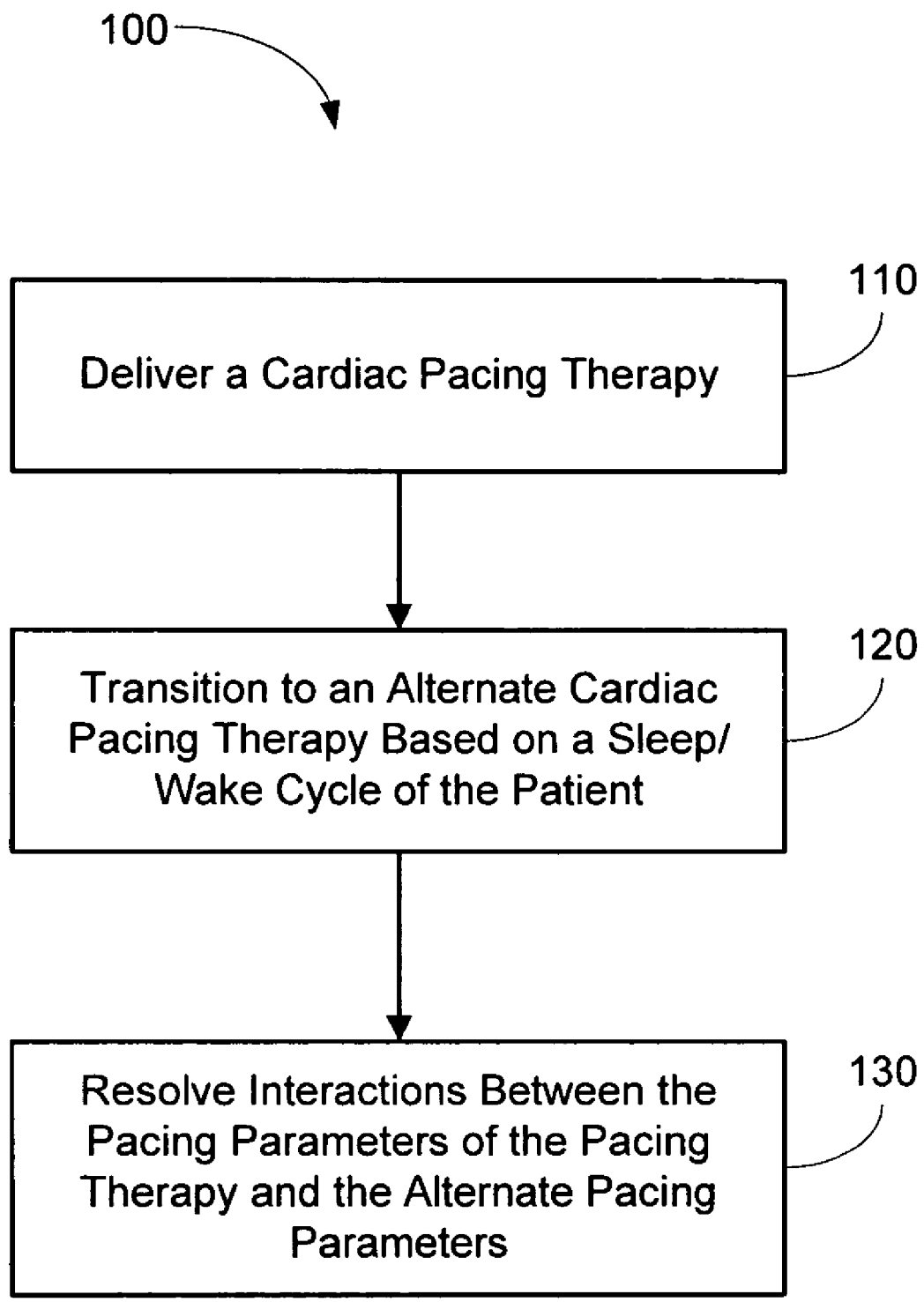
FIG. 1 illustrates a flowchart of a method for implementing sleep/wake cycle lower rate limit pacing adjustments in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings that form a part hereof, and in which are shown by way of illustration, various embodiments by which the invention may be practiced. It is to be understood that other embodiments may be utilized, and structural and functional changes may be made without departing from the scope of the present invention.

When cardiac pacing therapy is delivered to a patient, the pacing therapy is associated with various pacing parameters that control various aspects of therapy delivery. The pacing parameters may be programmable and may include, for example, a lower rate limit (LRL) which is associated with a minimal pacing rate that the pacemaker will pace at in the absence of intrinsic events. The LRL corresponds to the longest escape interval that the pacemaker will continuously implement. Upon delivery of a pacing pulse, the pacemaker initiates an escape interval. The escape interval is the period of time that the pacemaker will delay before delivering the next scheduled pacing pulse. If an intrinsic event is sensed before expiration of the escape interval, the pacemaker inhibits the delivery of the scheduled pacing pulse and restarts the escape interval.

In addition to the LRL pacing constraint, the pacing rate delivered by a pacemaker may be automatically adjusted based on information from a metabolic sensor that detects the patient's level of exertion or hemodynamic need. For example, when the metabolic sensor detects that the patient's level of activity has increased, the pacemaker automatically increases the pacing rate. The pacing rate may be increased, for example, from the LRL to a higher rate that corresponds to the patient's level of activity. The device continues to deliver pacing at the higher rate until the patient's activity level decreases, at which time the pacing rate is correspondingly lowered toward the LRL.

Human physiology is linked to a 24 hour clock known as the circadian rhythm. A number of biological processes modulate according to this internal clock. During sleep, the patient's metabolic functions slow down, respiration becomes deeper, and heart rate slows. In one scenario, the pacemaker may mimic the patient's physiological response to sleep by transitioning from a higher pacing rate to a lower pacing rate.

In some situations, slower pacing during sleep may not be desirable. For example, sleep may be linked to an increased likelihood of cardiac arrhythmia. Some patients are predisposed to nocturnal cardiac paroxysms associated with surges in vagal activity. A higher rate of pacing may be implemented to prevent the occurrence of arrhythmia during sleep. Further, sleep may be associated with increased respiratory disruptions, such as sleep apnea. Studies have shown that overdrive pacing during sleep may be an effective treatment for sleep apnea.

Embodiments of the invention involve transitioning between different pacing therapies at different times of the day and in concert with the patient's circadian rhythm. For example, FIG. 1 is a flowchart illustrating a method 100 for transitioning between different pacing therapies. A primary pacing therapy associated with a first set of parameters, including a primary lower rate limit, may be delivered 110 when the patient is awake. The device may transition 120 to an alternate pacing therapy associated with a second set of pacing parameters, including an alternate lower rate limit, when the patient is asleep. The primary and/or alternate pacing therapies may involve rate adaptive pacing wherein the patient's pacing rate above a lower rate limit is determined based on sensed activity or hemodynamic need.

The device resolves 130 interactions between the pacing parameters of the primary therapy and those of the alternate therapy. Resolving interactions may include, for example, arbitrating between the primary LRL and the alternate (LRL) used for rate adaptive pacing. Further, transitioning between primary and alternate pacing therapies may involve resolving interactions between additional pacing parameters, including, for example, lower rate hysteresis (LRH) and/or sensor rate hysteresis (SRH).

A hysteresis rate is an indication that the escape rate is a function of the history of the rate. For example, if the last event was a pace pulse, then the escape rate for the next cardiac cycle is equal to the programmed value of the lower rate. If the last event was a sensed intrinsic event, the escape rate is lower than the lower rate by a predetermined amount, e.g., 10 bpm. The rate hysteresis is often expressed as a difference in quantity or a fixed quantity in pulses per minute. Lower rate hysteresis and/or sensor rate hysteresis are implemented to allow the heart to beat via spontaneous, intrinsic contractions rather than as a result of pacing.

In accordance with embodiments of the invention, the patient's pacing rate may transition back and forth between a primary pacing therapy and an alternate pacing therapy based on the patient's circadian rhythm or sleep/wake cycle. The patient's sleep/wake cycle may be determined by various methodologies. In one implementation, the pacemaker circuitry may include a time of day clock. The patient's sleep and wake times may be programmed during an initialization stage. For example, the pacemaker may be programmed during an initialization period with times that correspond to implementation of the primary and/or alternate pacing therapies. For example, the pacemaker may be programmed to implement the primary (waking) therapy when the time of day clock indicates 7:00 a.m. and transition to the alternate pacing therapy when the time of day clock indicates 11:00 p.m. each day.

In another implementation, the patient or physician may communicate in real time with the pacemaker via a patient input device or other device to input information. Using such a device, the patient can indicate that he or she is going to sleep or has awakened. Directly entering sleep information allows for increased flexibility in implementing the pacing therapy transitions to correspond more closely to the patient's actual sleep/wake cycle.

In yet another implementation, the device may be equipped with sensors and supporting circuitry for automatically identifying when the patient is asleep and when the patient wakes up. Detecting the patient's sleep/wake cycle may be accomplished by examining transitions in heart rate, activity level, and/or respiration, for example. Methods and systems for detecting sleep/wake cycles, aspects of which may be utilized in the embodiments described herein, are discussed in commonly owned U.S. patent application Ser. No. 10/309,771, filed Dec. 4, 2000, now U.S. Pat. No. 7,189,204 and incorporated herein by reference.

In yet another implementation, pacing therapy transitions may be based on certain events that occur during sleep. For example, a pacing therapy transition may occur when the patient's shifts to or from a particular sleep stage, such as a rapid eye movement (REM) sleep stage, a non-REM sleep stage, or a state of autonomic arousal. Detection of REM and non-REM sleep stages is described in commonly owned U.S. patent application Ser. No. 10/643,006, filed Aug. 18, 2003, now U.S. Publication No. 2005/0043652 and incorporated herein by reference. Detection of autonomic arousal is described in commonly owned U.S. patent application Ser. No. 10/920,675, filed Aug. 17, 2004, now U.S. Publication No. 2005/0076908 and incorporated herein by reference. In some implementations, as described in U.S. patent application Ser. No. 10/643,006, the alternate pacing therapy may involve various diagnostic or test procedures that are performed which the patient is asleep to provide diagnostic information about the patient or information about the pacemaker functions.

In some embodiments, pacing therapy transitions may be triggered, for example, when the device detects physiological parameters indicative of sleep disordered breathing or other sleep related events. Methods and systems for detection of sleep disordered breathing, aspects of which may be implemented in the embodiments of the present invention, are described in commonly owned U.S. patent application Ser. No. 10/309,770, filed Dec. 4, 2002, now U.S. Pat. No. 7,252,640 and incorporated herein by reference.

In some embodiments, the pacemaker may incorporate circuitry to more fully monitor the patient's sleep quality conditions during sleep. For example, the device may be equipped with circuitry to implement a medical event logbook and/or a sleep logbook that may track various aspects of sleep quality and/or analyzes sleep-related events. In these embodiments, pacing therapy transitions may be triggered based on the state of the patient's sleep quality and/or other sleep related events, such as when the patient's disordered breathing corresponds to a particular apnea/hypopnea index, for example. Methods and systems for tracking sleep quality and sleep related events are described in the following commonly owned U.S. patent applications, all of which are incorporated herein by reference: Ser. No. 10/642,998, filed Aug. 18, 2003; now U.S. Publication No. 2005/0042589; Ser. No. 11/012,430, filed Dec. 15, 2004, now U.S. Publication No. 2006/0129193; and Ser. No. 10/920,568, filed Aug. 17, 2004, now U.S. Publication No. 2005/0080348.

In an exemplary embodiment, the alternate pacing therapy involves a different LRL from the primary pacing therapy. Adjusting the pacing LRL based on a patient's sleep/wake cycle can be beneficial to a patient because alternate pacing rates can be implemented at specific times of the day. Integrating an alternate sleep-time pacing lower rate limit, which is either greater than or less than a normal pacing lower rate limit, can be advantageous for patients who benefit from a higher pacing rate for sleep apnea treatment, and/or a lower pacing rate during sleep to more closely mimic the patient's circadian or diurnal rhythm.

When the alternate sleep-time LRL is implemented by the pacemaker, the pacemaker transitions the pacing therapy to correspond with the sleep-time LRL parameter. For example, if the alternate sleep-time LRL is programmed to be activated at the patient's normal sleep time as indicated by a time of day clock, the alternate sleep-time LRL becomes active at the appropriate time and the sensor rate and/or other rate drivers are adjusted to account for the alternate sleep-time LRL. When the patient's wake time occurs, as indicated by the time of day clock, the pacing rate is transitioned from the alternate (sleep-time) LRL to the primary (wake-time) LRL. The transition period can be abrupt or gradual. During the time that the alternate LRL is active, the pacemaker arbitrates between competing parameters of the primary pacing therapy and the alternate pacing therapy as described herein.

Figure 2:
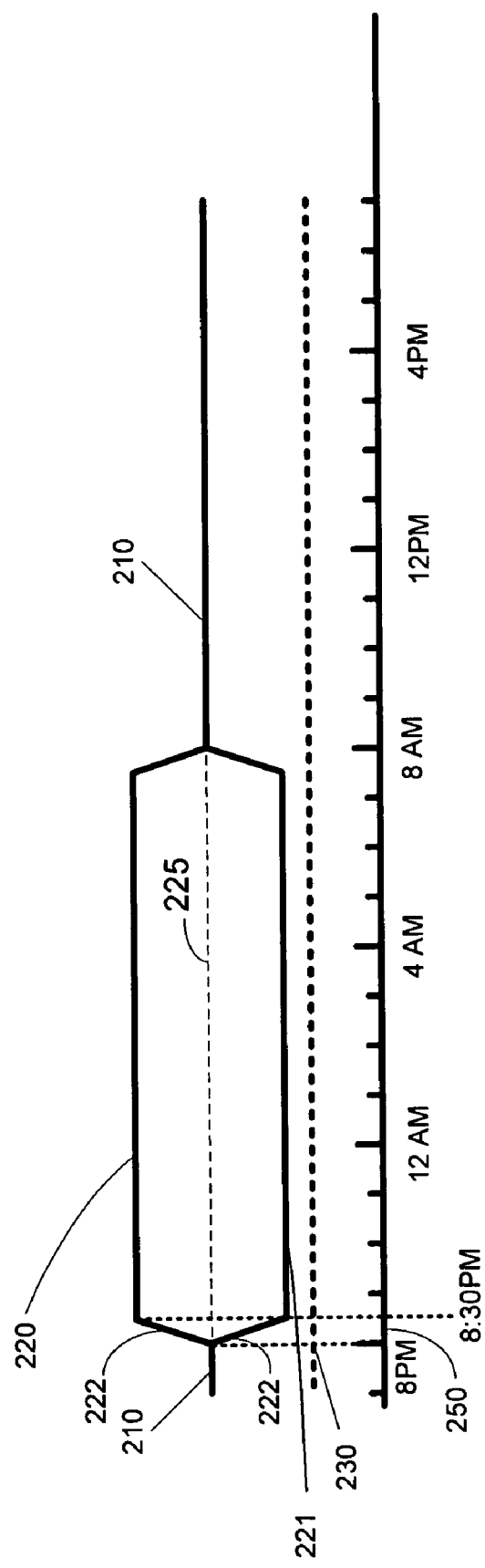
FIG. 2 is a graph illustrating lower rate limits over a 24-hour period of time in accordance with embodiments of the invention.

FIG. 2 is a graph illustrating example LRLs that may be implemented over a 24-hour period of time. The primary lower rate limit 210 is active at least during times of patient wakefulness. At a patient's bedtime, such as at 8 PM, the lower rate limit 210 is transitioned to an alternate sleep-time lower rate limit. The alternate LRL may be higher 220 or lower 221 than the primary LRL 210.

As indicated in FIG. 2 the adjustment from the primary pacing therapy associated with the primary LRL 210 to the alternate pacing therapy associated with the alternate LRL occurs during a transition period 250. During the transition period the pacemaker may smoothly transition from using the primary wake-time lower rate limit 210 to the alternate sleep-time lower rate limit 220, 221 over a period of time, such as between about 5 minutes and about 2 hours with a preferred transition time of about 30 minutes. Thus, as illustrated in FIG. 2, at 8 p.m., the primary LRL 210 is active. Between 8 PM and 8:30 PM the LRL 222 is in a period of gradual transition. At 8:30 PM the alternate LRL 220, 221 is active.

Figure 3A:
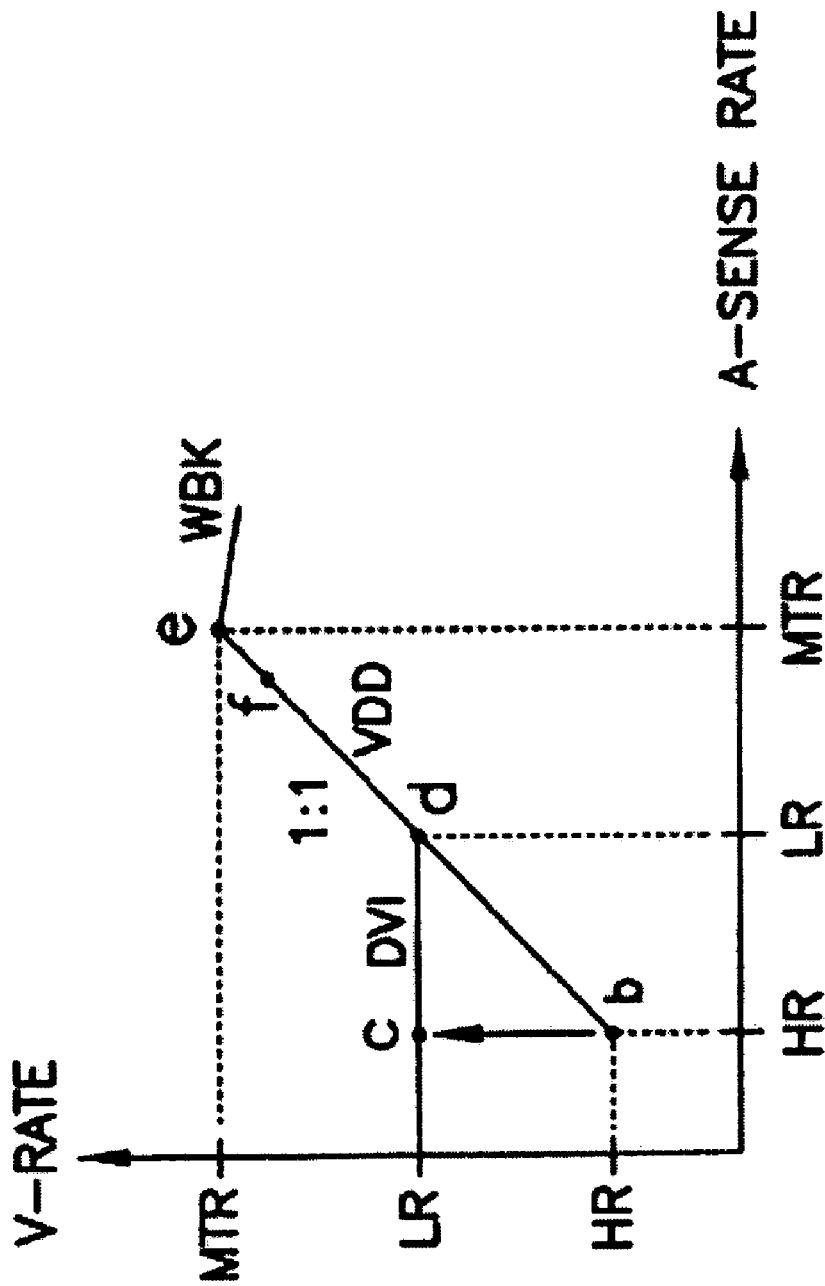
FIGS. 3A and 3B are transfer function graphs illustrating a lower rate limit, lower rate hysteresis, and sensor rate hysteresis that may be utilized in transitioning from a pacing therapy to an alternate pacing therapy in accordance with embodiments of the invention.
Figure 3B:
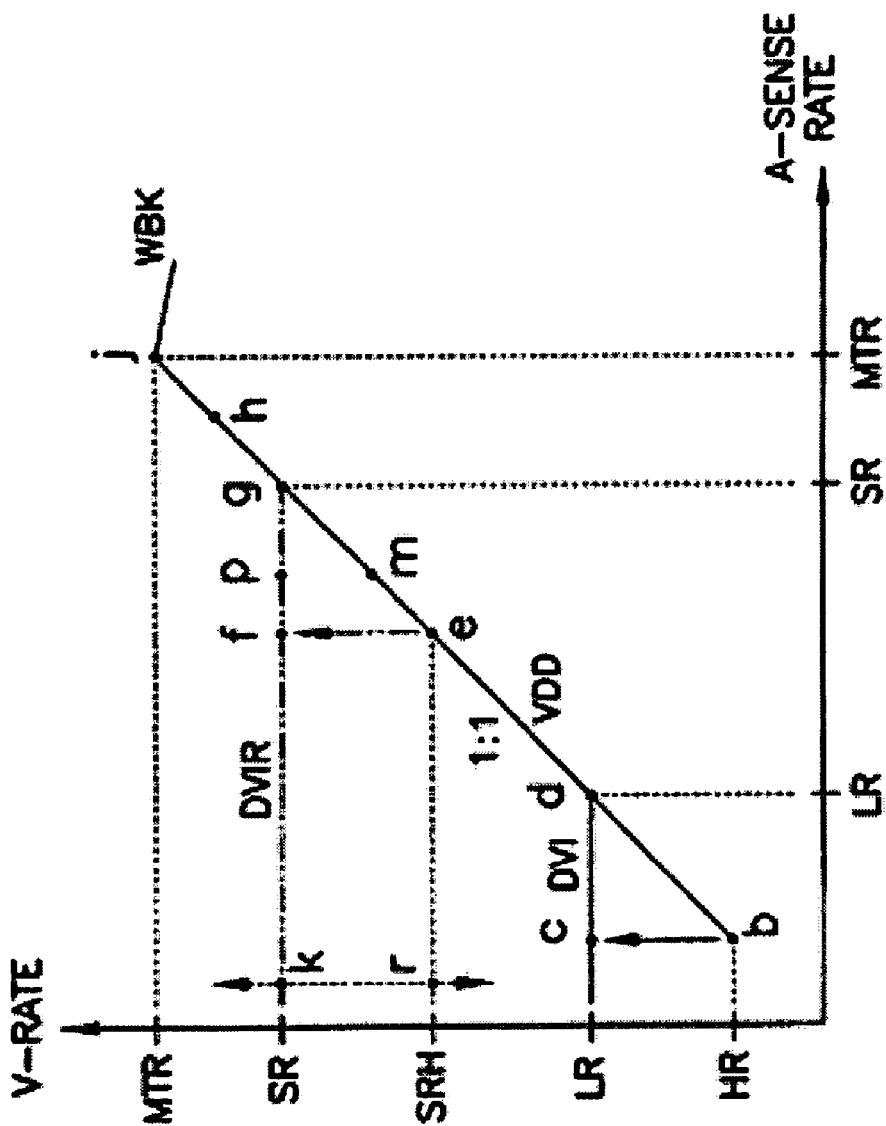

The LRL of a pacing therapy may be associated with a lower rate hysteresis 230, illustrated in FIG. 2 and discussed further in connection with FIGS. 3A and 3B. FIGS. 3A and 3B are transfer function graphs illustrating the pacing behavior of a dual chamber pacemaker operating in DDDR mode. In this mode, the pacemaker is capable of sensing and pacing both atrial and ventricular chambers. The pacemaker may trigger a pacing pulse or inhibit delivery of a scheduled pacing pulse based on sensed events. Further, the pacemaker operates in a rate responsive pacing mode such that the pacing rate is controlled by a metabolic sensor. The rate responsive pacing rate may be subject to a sensor hysteresis rate as described in connection with FIG. 3B.

FIG. 3A provides a diagrammatic representation of the transfer function of a DDD pacemaker operating with a lower rate hysteresis. In FIG. 3A, the atrial sense (A-sense) rate is shown as the abscissa and the ventricular sense (V-sense) rate is shown as the ordinate of the graph. In the atrial tracking range of operation of the pacemaker (point b to point e ), there is 1:1 tracking between A-sense and a V-pace. That is, each A-sense is followed by a V-pace, one AV (atrial-ventricular) delay interval later, i.e., operation is VDDx behavior. If the A-sense rate were gradually reduced from point e until it was at point b, the V-paces would track the A-senses 1:1 over this range. When the A-sense rate became lower than the hysteresis rate (point b), the pacemaker system would switch to an escape rate equal to the lower rate (point c). There can be one or more A-paces at the point b, which causes the switch to the V-rate at point c. The operating behavior would now be DVI, that is, an A-pace followed by a V-pace at the lower rate.

As the A-sense rate is increased from point c, the escape rate would stay at the lower rate until the A-sense rate reached point d. Thereafter, the escape rate would follow the 1:1 curve, past the point d and up to point e.

The triangle defined by points b-c-d is referred to as the lower rate hysteresis loop. The length of the line b-c is usually expressed as a constant value of rate ($\Delta HR$). The length of the line could also be expressed as a function of the rate or as a function of the interval, such as a percentage of the interval.

FIG. 3B further illustrates sensor rate hysteresis in DDDR Mode. If the sensor rate (SR) is less than the LRL, the pacemaker system would switch to an escape rate equal to the lower rate (point c). If the sensor value (SV) increases, the SR will then increase. This results in line g-k being located at a higher point in the graph as illustrated in FIG. 3B. In real terms, this indicates that the sensor rate can be much higher than the A-pulse rate, and the actual demands of the patient may not be met by the atrial function. If the A-sense rate was reduced from point h, the V-rate will track the A-sense rate past point g and down to point e. For A-sense rates below point e, the behavior of the pacemaker will switch to point f. Pacing behavior will be DVIR with an escape rate equal to the SR. As the A-sense rate is reduced further, the operation of the pacemaker will follow line f-k. If the A-sense rate were to increase, operation of the pacemaker would follow line k-g. For A-sense rates above g, the operation of the pacemaker will follow line g-j.

Line e-f is the amount of sensor rate hysteresis. It is often expressed as a delta value of rate, but other values as described above for lower rate hysteresis may also be used. The triangle described by e-f-g is the sensor rate hysteresis loop. Note that the lines k-g and c-f shift up and down with the sensor value. If the system is operating at point p and the sensor rate was reduced, operating behavior would remain as DVIR until the sensor rate reached point m. At point m, behavior would switch to VDDR, and as the SR continued to decrease, operation of the pacemaker would follow line m-b. At point b, the operation of the pacemaker would switch back up to point c. Pacemaker operation including hysteresis rates that may be utilized in embodiments of the invention is described in commonly owned U.S. Pat. No. 5,891,175 which is incorporated herein by reference.

As previously mentioned, transitioning from a primary therapy to an alternate therapy in accordance with embodiments of the invention may involve arbitrating between pacing parameters associated with the primary therapy and the pacing parameters associated with the alternate pacing therapy. In some implementations, this involves arbitrating between a pacing rate indicated by the primary pacing therapy and a pacing rate indicated by the alternate pacing therapy. For example, the lower pacing rate of the alternate therapy may be in conflict with a lower rate hysteresis and/or a sensor rate hysteresis, requiring arbitration between the alternate LRL and the primary lower rate hysteresis or sensor rate hysteresis.

Figure 4:
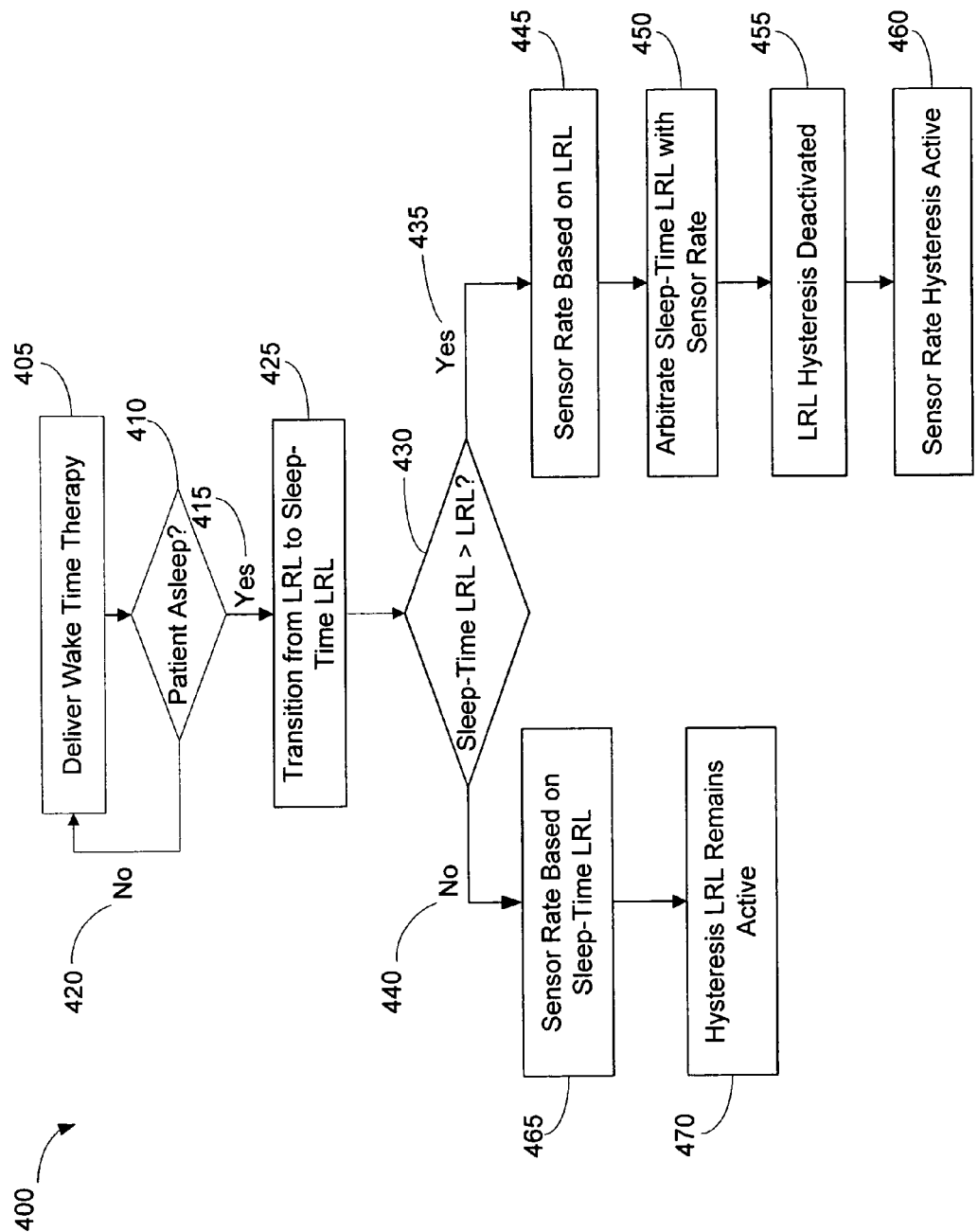
FIG. 4 is a flowchart of a method for adjusting pacing parameters according to a patient's sleep/wake cycle in accordance with embodiments of the invention.

FIG. 4 is a flowchart of a method 400 for adjusting pacing parameters in concert with a patient's sleep/wake cycle in accordance with embodiments of the invention. As illustrated in FIG. 4, a wake-time therapy is delivered 405 having parameter values for a sensor rate, a LRL, a lower rate hysteresis and a sensor rate hysteresis, for example. The system determines 410 if the patient is asleep. The sleep determination 410 can be a result of an arbitrary patient sleep setting, e.g., where the sleep cycle is programmed to last from 11 p.m. to 7 a.m., or other time period. Patient sleep can be detected using one or more sensors indicative of patient activity or by using other methods.

If the patient is not asleep 420, wake time therapy continues to be delivered 405 until sleep is detected. Once the determination is made that the patient is asleep 415, the LRL of the pacing rate is transitioned 425 from a primary wake-time LRL to an alternate sleep-time LRL. Transitioning between the primary LRL and the sleep-time lower rate limit can be gradual or abrupt and can span a period from anywhere between about five minutes to about two hours, with a preferable transition period of 30 minutes. However, if the sensor pacing rate is significantly above the LRL, the transition to the sleep-time LRL may be delayed until the rate decreases.

During transition, adjustments may be made so that rate adaptive pacing utilizes the sleep-time LRL parameter. Accordingly, in the sleep-time mode, a determination 430 is made as to whether the alternate LRL is higher than the primary LRL. If the alternate LRL is higher 435 than the primary LRL, the pacemaker adjusts pacing so that the sensor rate is based 445 on the primary LRL. The alternate LRL is arbitrated 450 with the sensor indicated rate. Arbitration of the alternate LRL with the sensor indicated rate may involve, for example, delivering pacing therapy to the patient at a rate corresponding to the greater of the alternate LRL and the sensor indicated rate. If the alternate LRL is greater than the primary LRL 435, the pacemaker adjusts so that the LRL hysteresis is deactivated 455, but the sensor rate hysteresis remains active 460. In this scenario, the lower rate hysteresis would be disabled because it is undesirable to lower the pacing rate when the alternate LRL is active and is higher than the primary LRL.

When the alternate LRL is not 440 higher than the primary LRL the pacemaker adjusts the rate adaptive pacing so that the sensor rate is based 465 on the alternate LRL and the lower rate hysteresis remains active 470 so long as the alternate LRL is greater than the lower rate hysteresis.

Automatically resolving pacing parameter interactions during and/or after transitioning from a primary pacing therapy to an alternate pacing therapy is desirable for integrating a circadian or apnea therapy during periods of sleep into the patient's overall pacing regimen. Implementing algorithms to automatically arbitrate between competing parameters provides the desired pacing rate to the patient while reducing the degree of complexity required for proper initialization of the pacing rate transitions.

Figure 5:
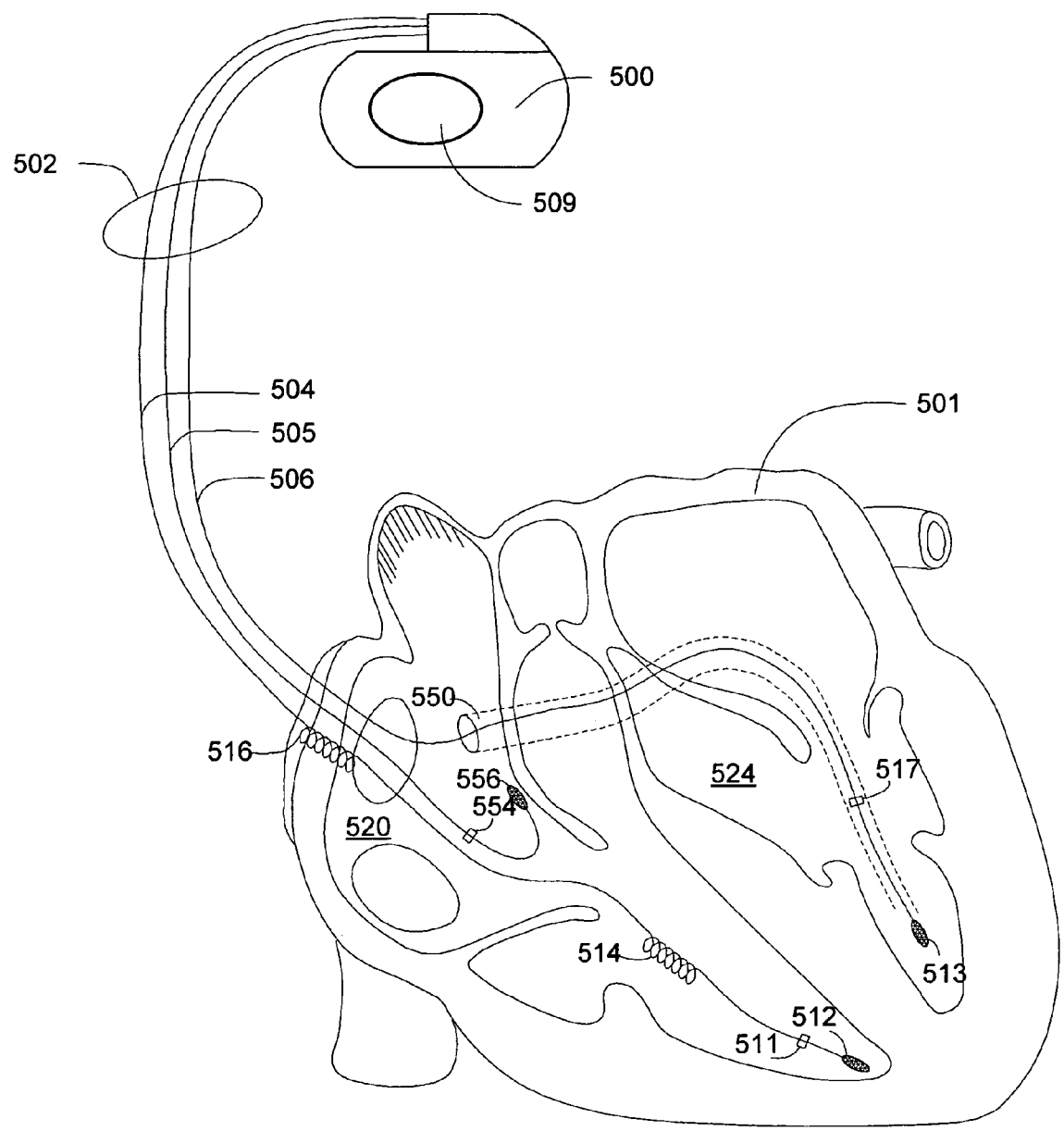
FIG. 5 is a partial view of a cardiac rhythm management (CRM) device that may be used to implement time of sleep/wake cycle pacing rate adjustments in accordance with embodiments of the invention.

FIG. 5 is a partial view of a cardiac rhythm management (CRM) device that may be used to implement pacing rate adjustments based on sleep/wake cycle in accordance with embodiments of the invention. Methods of the invention may be implemented in a variety of implantable or patient-external cardiac therapeutic and/or diagnostic devices including, for example, pacemakers, pacemaker/defibrillators, bi-ventricular pacemakers, and/or cardiac resynchronization devices, among others. The CRM device illustrated in FIG. 5 includes an implantable housing 500 containing circuitry electrically coupled to an intracardiac lead system 502. Portions of the implantable housing may be configured as a can electrode 509. The housing 500 and the intracardiac lead system 502 is implanted in a human body with portions of the intracardiac lead system 502 inserted into a heart 501. The intracardiac lead system 502 is used to detect electric cardiac signals produced by the heart 501 and to provide electrical energy to the heart 501 under predetermined conditions to treat cardiac arrhythmias.

The intracardiac lead system 502 includes one or more electrodes used for pacing, sensing, and/or defibrillation. In the particular embodiment shown in FIG. 5, the intracardiac lead system 502 includes a right ventricular lead system 504, a right atrial lead system 505, and a left ventricular lead system 506. In one embodiment, the right ventricular lead system 504 is configured as an integrated bipolar pace/shock lead.

The right ventricular lead system 504 includes an SVC-coil 516, an RV-coil 514, and an RV-tip electrode 512. The RV-coil 514, which may alternatively be configured as an RV-ring electrode 511 and an RV-coil 514, is spaced apart from the RV-tip electrode 512, which is a pacing electrode for the right ventricle.

The right atrial lead system 505 includes a RA-tip electrode 556 and an RA-ring electrode 554. The RA-tip 556 and RA-ring 554 electrodes may provide pacing pulses to the right atrium of the heart and may also be used to detect cardiac signals from the right atrium. In one configuration, the right atrial lead system 505 is configured as a J-lead.

In the configuration of FIG. 5, portions of the intracardiac lead system 502 are shown positioned within the heart 501, with the right ventricular lead system 504 extending through the right atrium and into the right ventricle. Typical locations for placement of the RV-tip electrode 512 are at the right ventricular (RV) apex or the RV outflow tract.

In particular, the RV-tip electrode 512 and RV-coil electrode 514 are positioned at appropriate locations within the right ventricle. The SVC-coil 516 is positioned at an appropriate location within a major vein leading to the right atrium chamber of the heart 501. The RV-coil 514 and SVC-coil 516 depicted in FIG. 5 are defibrillation electrodes.

The left ventricular lead system 506 is advanced through the superior vena cava (SVC), the right atrium 520, the ostium of the coronary sinus, and the coronary sinus 550. The left ventricular lead system 506 is guided through the coronary sinus 550 to a coronary vein of the left ventricle 524. This vein is used as an access pathway for leads to reach the surfaces of the left atrium and the left ventricle which are not directly accessible from the right side of the heart. Lead placement for the left ventricular lead system may be achieved via subclavian vein access and a preformed guiding catheter for insertion of the left ventricular (LV) electrodes 513 and 517 adjacent the left ventricle. In one configuration, the left ventricular lead system 506 is implemented as a single-pass lead.

An LV distal electrode 513, and an LV proximal electrode 517 may be positioned adjacent to the left ventricle. The LV proximal electrode 517 is spaced apart from the LV distal electrode, 513 which is a pacing electrode for the left ventricle. The LV distal 513 and LV proximal 517 electrodes may also be used for sensing the left ventricle.

The lead configurations illustrated in FIG. 5 represent one illustrative example. Additional lead/electrode configurations may include additional and/or alternative intracardiac electrodes and/or epicardial electrodes. For example, in one configuration, an extracardiac lead may be used to position epicardial electrodes adjacent the left atrium for delivering electrical stimulation to the left atrium and/or sensing electrical activity of the left atrium.

Figure 6:
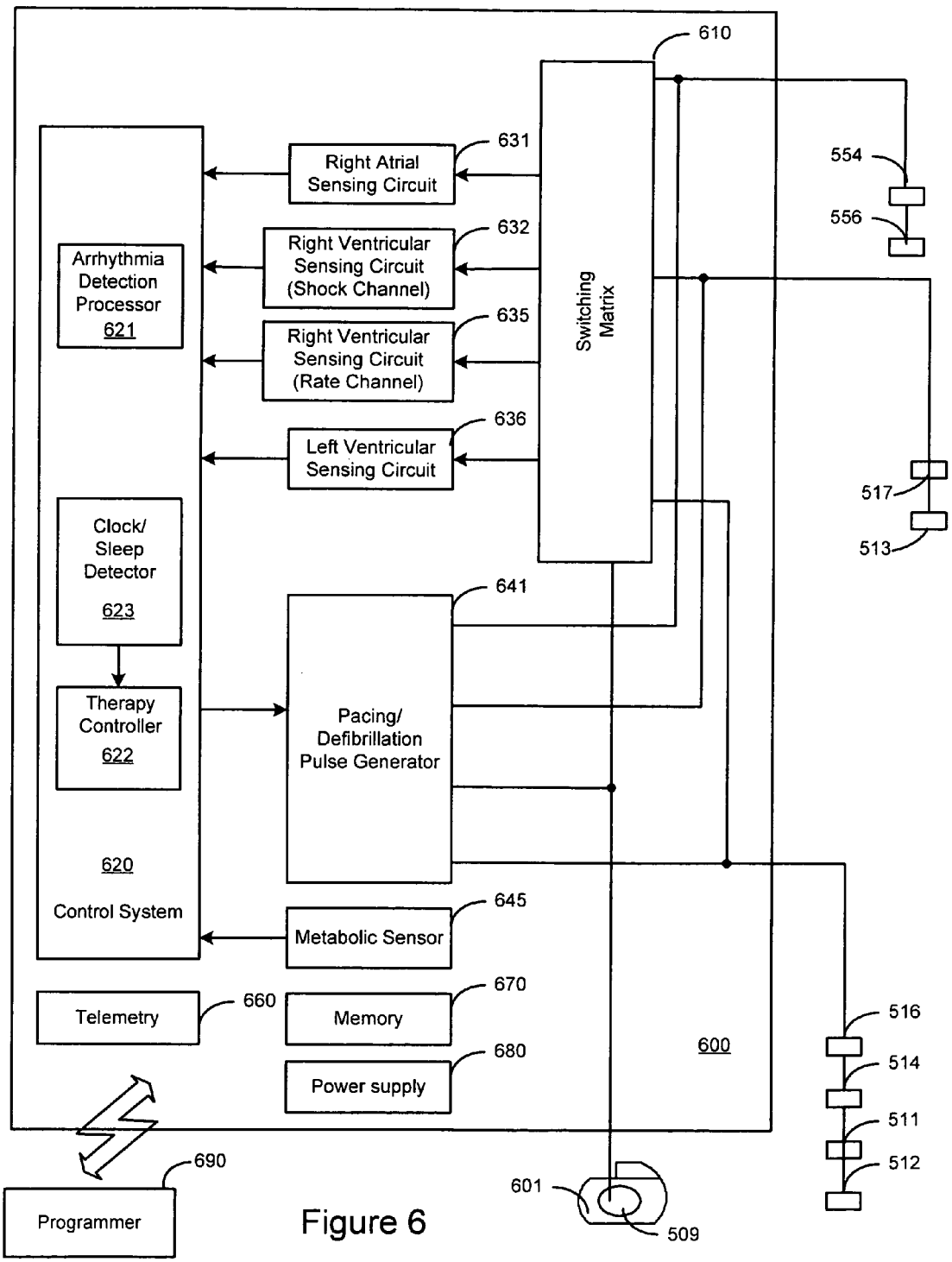
FIG. 6 is a block diagram of a cardiac rhythm management (CRM) device suitable for implementing sleep/wake cycle pacing rate adjustments in accordance with embodiments of the invention.

Referring now to FIG. 6, there is shown a block diagram of a cardiac rhythm management (CRM) device 600 suitable for implementing sleep/wake cycle pacing rate adjustments in accordance with embodiments of the invention. FIG. 6 shows a CRM device 600 divided into functional blocks. It is understood by those skilled in the art that there exist many possible configurations in which these functional blocks can be arranged. The example depicted in FIG. 6 is one possible functional arrangement. Various functions of the CRM device 600 may be accomplished by hardware, software, or a combination of hardware and software.

The CRM device 600 includes components for sensing cardiac signals from a heart and delivering therapy, e.g., pacing pulses or defibrillation shocks, to the heart. The circuitry of the CRM device 600 may be encased and hermetically sealed in a housing 601 suitable for implanting in a human body. Power to the circuitry is supplied by an electrochemical battery power supply 680 that is enclosed within the housing 601. A connector block with lead terminals (not shown) is additionally attached to housing 601 to allow for the physical and electrical attachment of the intracardiac lead system conductors to the encased circuitry of the CRM device 600.

In one embodiment, the CRM device 600 comprises programmable microprocessor-based circuitry, including control circuitry 620, a memory circuit 670, sensing circuitry 631, 632, 635, 636, and a pacing/defibrillation pulse generator 641. Components of the CRM device 600 cooperatively perform operations involving time of day pacing adjustments according to the approaches of the present invention. The control circuitry 620 may include a clock or a sleep processor 623 for implementing time of day therapy control.

A clock may be utilized for determining the sleep/wake cycle based on programmed sleep times and wake times, for example. Alternatively, or additionally, the sleep processor may acquire additional information associated with patient sleep. For example, the sleep processor may comprise a sleep detector configured to sense that the patient is asleep and sense that the patient is awake. In another configuration, the sleep processor may include additional circuitry and sensors to detect sleep stages, sleep disturbances, such as disordered breathing, and sleep quality.

A therapy controller 622 includes circuitry that controls the transition from a primary pacing therapy to an alternate pacing therapy. Further the therapy controller 622 includes arbitration circuitry for arbitrating between conflicting therapy parameters.

The control circuitry 620 may encompass various functional components, for example, an arrhythmia classification processor 621 for detecting cardiac conditions such as bradycardia and a therapy control unit 622 for controlling pacing therapy and arbitrating between pacing therapies.

The memory circuit 670 may store program instructions used to implement the functions of the CRM device 600 as well as data acquired by the CRM device 600. For example, the memory circuit 670 may store historical records of sensed cardiac signals, including arrhythmic episodes, and/or information about therapy delivered to the patient. The memory circuit 670 may also store historical patient sleep-time information, parameter adjustment information including rate adjustment transition data.

The historical data stored in the memory 670 may be used for various purposes, including diagnosis of patient diseases or disorders. Analysis of the historical data may be used to adjust the operations of the CRM device 600. Data stored in the memory 670 may be transmitted to an external programmer unit 690 or other computing device, such as an advanced patient management system as needed or desired.

Telemetry circuitry 660 allows the CRM device 600 to communicate with an external programmer unit 690 and/or other remote devices. In one embodiment, the telemetry circuitry 660 and the external programmer unit 690 use a wire loop antenna and a radio frequency telemetric link to receive and transmit signals. In this manner, programming commands and data may be transferred between the CRM device 600 and the external programmer 690 after implant.

The CRM device 600 may function as a pacemaker and/or a defibrillator. As a pacemaker, the CRM device 600 delivers a series of electrical stimulations to the heart to regulate heart rhythm. Therapy control circuitry 622 controls the delivery of pacing pulses to treat various arrhythmic conditions of the heart, for example. In various embodiments, the CRM device 600 may deliver pacing pulses to one or more of the right atrium, left atrium, right ventricle and the left ventricle. The heart may be paced to treat bradycardia, or to synchronize and/or coordinate contractions of the right and left ventricles.

For example, right ventricular pacing may be implemented using unipolar or bipolar configurations. Unipolar RV pacing involves, for example, pacing pulses delivered between the RV-tip 512 to can 509 electrodes. Bipolar pacing involves, for example, delivery of pacing pulses between the RV-tip 512 to RV-coil 514 electrodes. If an RV-ring electrode 511 is present, bipolar pacing may be accomplished by delivering the pacing pulses to the RV-tip 512 and RV-ring 511 electrodes.

Left ventricular pacing may be implemented using unipolar or bipolar configurations. Unipolar LV pacing may include, for example, pacing pulses delivered between the LV distal electrode 513 and the can 509. Alternatively, bipolar LV pacing may be accomplished by delivering the pacing pulses using the LV distal electrode 513 and the LV proximal electrode 517.

Similarly, unipolar (RA-tip electrode 556 to can electrode 509) atrial pacing or bipolar (RA-tip electrode 556 to RA-ring electrode 554) atrial pacing may be provided by the CRM device 600.

In accordance with the present invention, the therapy controller 622 may be programmed to adjust pacing parameters when pacing one or more of the right atrium, left atrium, right ventricle and the left ventricle based on a patient's sleep/wake cycle. Furthermore, the therapy controller circuitry 622, in accordance with the present invention, may adjust the pacing based on the sleep-time information acquired from the clock or sleep detector 623. For example, the therapy control circuitry 622 can arbitrate among competing parameters of a primary therapy and an alternate therapy. The therapy controller 622 can implement gradual or abrupt transitions between a primary pacing therapy and an alternate, sleep-time pacing therapy, for example.

The CRM device 600 may also provide tachyarrhythmia therapy. For example, tachyarrhythmia therapy may be provided in the form of anti-tachycardia pacing (ATP) pulses delivered to the heart. The ATP pulses may involve a series of timed paces of programmable width and amplitude that are implemented to interrupt a tachyarrhythmia episode. The ATP therapy may involve, for example, burst pacing at about 25 Hz to about 50 Hz. In various implementations, the pace-to-pace interval may have a variable or constant length. For immediately life threatening arrhythmias, such as ventricular fibrillation, the therapy control circuitry 622 may control the delivery of one or a series of defibrillation shocks to the heart to terminate the fibrillation.

In the embodiment depicted in FIG. 6, electrodes RA-tip 556, RA-ring 554, RV-tip 512, RV-ring 611, RV-coil 514, SVC coil 516, LV distal electrode 513, LV proximal electrode 517, and can 509 are coupled through a switching matrix 610 to various sensing circuits 631, 632, 635, 636. A right atrial sensing channel circuit 631 serves to sense and amplify electrical signals from the right atrium of the heart. For example, bipolar sensing in the right atrium may be implemented by sensing signals developed between the RA-tip 556 and RA-ring 554 electrodes. The switch matrix 610 may be operated to couple the RA-tip 556 and RA-ring 554 electrodes to the RA sensing channel circuit 631 to effect bipolar sensing of right atrial signals. Alternatively, unipolar right atrial sensing may be accomplished by operating the switch matrix 610 to couple the RA-tip 556 and can 509 electrodes to the RA sensing channel circuit 631.

Cardiac signals sensed through the use of the RV-tip electrode 512 are right ventricular (RV) near-field signals and are referred to as RV rate channel signals herein. Bipolar rate channel sensing may be accomplished by operating the switch matrix 610 to couple the RV-tip 512, RV-ring 511 and the RV-coil electrodes 514 through the RV rate channel sensing circuitry 635. The rate channel signal may be detected, for example, as a voltage developed between the RV-tip 512 and the RV-coil 514 electrodes. The RV rate channel sensing circuitry 635 serves to sense and amplify the RV rate channel signal.

Unipolar RV sensing may be implemented, for example, by coupling the RV-tip 512 and can 509 electrodes to the RV rate channel sensing circuitry 635. In this configuration, the rate channel signal is detected as a voltage developed between the RV-tip 512 to can 509 sensing vector.

The RV lead system may also include an RV-ring electrode (not shown in FIG. 6) used for bipolar pacing and sensing. If an RV-ring electrode is included in the lead system, bipolar sensing may be accomplished by sensing a voltage developed between the RV-tip 512 and RV-ring (not shown) electrodes.

Far-field signals, such as cardiac signals sensed through use of one of the defibrillation coils or electrodes 514, 516 and the can 509, or using both of the defibrillation coils or electrodes 514, 516, are referred to as morphology or shock channel signals herein. The shock channel signal may be detected as a voltage developed between the RV-coil 514 to the can electrode 509, the RV-coil 514 to the SVC-coil 516, or the RV-coil 514 to the can electrode 509 shorted to the SVC-coil 516. The switch matrix 610 is operated to couple the desired shock channel sensing vector, e.g., RV-coil to can, to the right ventricular shock channel sensing circuitry 632. The RV shock channel sensing circuitry 632 serves to sense and amplify the shock channel signal.

The outputs of the switching matrix 610 may also be operated to couple selected combinations of the electrodes to LV sensing channel circuitry 636 for sensing electrical activity of the left ventricle. Bipolar left ventricular sensing may be accomplished by operating the switch matrix 610 to couple the LV-distal 513 and the LV proximal electrodes 517 through the LV channel sensing circuitry 636. In this configuration, the LV signal is detected as a voltage developed between the LV proximal and LV distal electrodes.

Unipolar LV sensing may be implemented, for example, by coupling the LV distal 513 and can 509 electrodes to the LV sensing circuitry 636. In this configuration, the LV signal is detected as a voltage developed between the RV-tip 512 to can 509 sensing vector.

The CRM device 600 may incorporate one or more metabolic sensors 645 for sensing the activity and/or hemodynamic need of the patient. Rate-adaptive pacemakers typically utilize metabolic sensors to adapt the pacing rate to match the patient's hemodynamic need. A rate-adaptive pacing system may use an activity or respiration sensor to determine an appropriate pacing rate. Patient activity may be sensed, for example, using an accelerometer disposed within the housing of the pulse generator. Transthoracic impedance, which may be measured, for example, via the intracardiac electrodes, may be used to determine respiration rate. Sensor information from the metabolic sensor is used to adjust the pacing rate to support the patient's hemodynamic need. If the sensors indicate the patient's activity and/or respiration rate is high, then the patient's pacing rate is increased above a lower rate limit to correspond to the level of activity or rate of respiration.

It will, of course, be understood that various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method for delivering cardiac pacing therapy to a patient, comprising:
   delivering a primary cardiac pacing therapy associated with one or more primary pacing parameters, including a primary lower rate limit, and a sensor indicated pacing rate that is based on the primary lower rate limit;
   transitioning to an alternate cardiac pacing therapy associated with one or more alternate pacing parameters, including an alternate lower rate limit, the transition based on a sleep/wake cycle of the patient; and
   during delivery of the alternate cardiac pacing therapy, in response to the alternate lower rate limit being greater than the primary lower rate limit, resolving interactions between the primary pacing parameters of the primary pacing therapy and the alternate pacing parameters by selecting between pacing using the alternate pacing parameters and pacing using the sensor indicated rate which is based on the primary pacing parameters, the selecting based on a value of an alternate cardiac pacing parameter and a value of the sensor indicated rate.

2. The method of claim 1, wherein
   delivering the cardiac pacing therapy comprises delivering a rate adaptive pacing therapy using rate hysteresis; and
   selecting between pacing using the alternate pacing parameters and pacing using the sensor indicated rate comprises selecting between maintaining activation or deactivating the rate hysteresis.

3. The method of claim 1, wherein transitioning to the alternate cardiac pacing therapy is initiated by input from an external source.

4. The method of claim 1, wherein transitioning to the alternate cardiac pacing therapy comprises:
   detecting a change in a sleep/wake status of the patient; and
   transitioning to the alternate cardiac pacing therapy based on the change in the patient's sleep/wake status.

5. The method of claim 1, wherein selecting between pacing using the alternate pacing parameters and pacing using the sensor indicated rate that is based on the primary pacing parameters comprises using an alternate lower rate limit associated with the alternate cardiac pacing therapy during the alternate pacing therapy if the alternate lower rate limit is below a lower rate limit associated with the cardiac pacing therapy.

6. The method of claim 5, wherein resolving the interactions comprises using a lower rate hysteresis if the alternate lower rate limit associated with the alternate cardiac pacing therapy is below the lower rate limit associated with the primary cardiac pacing therapy.

7. The method of claim 1, wherein selecting between pacing using the alternate pacing parameters and pacing using the sensor indicated rate comprises using a lower rate limit associated with the primary cardiac pacing therapy during the alternate cardiac pacing therapy if an alternate lower rate limit associated with the alternate cardiac pacing therapy is above the lower rate limit.

8. The method of claim 7, wherein resolving the interactions between the primary pacing parameters of the primary cardiac pacing therapy and the alternate pacing parameters comprises disabling a lower rate hysteresis if the alternate lower rate limit is above the lower rate limit.

9. The method of claim 1, wherein resolving the interactions between the pacing parameters of the cardiac pacing therapy and the alternate pacing parameters comprises arbitrating between a pacing rate indicated by the alternate cardiac pacing therapy and a pacing rate indicated by the primary pacing therapy.

10. The method of claim 9, wherein arbitrating between the therapy interactions comprises arbitrating between a pacing rate indicated by the alternate cardiac pacing therapy and a lower rate hysteresis indicated by the primary cardiac pacing therapy.

11. The method of claim 9, wherein arbitrating between the therapy interactions comprises arbitrating between a pacing rate indicated by the alternate cardiac pacing therapy and a sensor rate hysteresis indicated by the primary cardiac pacing therapy.

* * * * *

UNITED STATES PATENT AND TRADEMARK OFFICE
CERTIFICATE OF CORRECTION

PATENT NO.         : 7,577,479 B2                                  Page 1 of 1
APPLICATION NO.    : 11/083136
DATED              : August 18, 2009
INVENTOR(S)        : Hartley et al.

It is certified that error appears in the above-identified patent and that said Letters Patent is hereby corrected as shown below:

<u>In the Specification:</u>

Col. 6, line 13: "Dec. 4, 2000," should read --Dec. 4, 2002,--.

Signed and Sealed this

Eighth Day of December, 2009

David J. Kappos
*Director of the United States Patent and Trademark Office*

UNITED STATES PATENT AND TRADEMARK OFFICE
CERTIFICATE OF CORRECTION

PATENT NO.       : 7,577,479 B2                                     Page 1 of 1
APPLICATION NO. : 11/083136
DATED            : August 18, 2009
INVENTOR(S)      : Hartley et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 226 days.

Signed and Sealed this

Fourteenth Day of December, 2010

David J. Kappos
*Director of the United States Patent and Trademark Office*